(12) United States Patent
Maeda et al.

(10) Patent No.: US 8,953,739 B2
(45) Date of Patent: Feb. 10, 2015

(54) IMAGE PROCESSING APPARATUS AND X-RAY CT SYSTEM

(75) Inventors: Tatsuo Maeda, Nasushiobara (JP); Manabu Hiraoka, Nasushiobara (JP); Naoko Toyoshima, Yokohama (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 13/107,511

(22) Filed: May 13, 2011

(65) Prior Publication Data

US 2011/0280366 A1 Nov. 17, 2011

(30) Foreign Application Priority Data

May 17, 2010 (JP) .................................. 2010-113607
Apr. 15, 2011 (JP) .................................. 2011-090948

(51) Int. Cl.
*A61B 6/03* (2006.01)
*A61B 6/00* (2006.01)
*G06T 7/00* (2006.01)
*A61B 6/02* (2006.01)

(52) U.S. Cl.
CPC .................. *A61B 6/032* (2013.01); *A61B 6/469* (2013.01); *A63B 6/503* (2013.01); *A61B 6/504* (2013.01); *A61B 6/5264* (2013.01); *A61B 6/541* (2013.01); *A61B 6/545* (2013.01); *G06T 7/0042* (2013.01); *G06T 2207/10116* (2013.01); *G06T 2207/20068* (2013.01); *G06T 2207/30061* (2013.01); *A61B 6/027* (2013.01)
USPC .............................................. 378/8; 382/131

(58) Field of Classification Search
USPC .................................... 378/4, 8; 382/128, 131
See application file for complete search history.

(56) References Cited

U.S. PATENT DOCUMENTS

| | | | | |
|---|---|---|---|---|
| 5,699,799 | A | * | 12/1997 | Xu et al. .................... 600/407 |
| 5,970,112 | A | * | 10/1999 | Hsieh .............................. 378/8 |
| 6,023,497 | A | * | 2/2000 | Takahashi et al. ............. 378/57 |
| 6,028,907 | A | * | 2/2000 | Adler et al. ..................... 378/4 |
| 6,421,413 | B1 | * | 7/2002 | Knoplioch et al. ............. 378/19 |
| 6,501,819 | B2 | * | 12/2002 | Unger et al. ...................... 378/5 |
| 6,501,848 | B1 | * | 12/2002 | Carroll et al. ................ 382/128 |
| 6,842,638 | B1 | * | 1/2005 | Suri et al. ...................... 600/425 |
| 7,260,170 | B2 | * | 8/2007 | Arenson et al. .................. 378/4 |

(Continued)

FOREIGN PATENT DOCUMENTS

| | | |
|---|---|---|
| JP | 2000-079110 | 3/2000 |
| JP | 2005-124895 | 5/2005 |

(Continued)

OTHER PUBLICATIONS

Deniz Aykac et al., Segmentation and Analysis of the Human Airway Tree From Three-Dimensional X-ray CT Images, IEEE Transactions on Medical Imaging, vol. 22, No. 8, Aug. 2003, pp. 940-950.

(Continued)

*Primary Examiner* — Hoon Song
(74) *Attorney, Agent, or Firm* — Oblon, Spivak, McClelland, Maier & Neustadt, L.L.P.

(57) ABSTRACT

An image processing apparatus and X-ray CT system, having a tracheal bifurcation area extraction part, for extracting the tracheal bifurcation area from an X-ray image and a tracheal bifurcation identification part, for identifying the tracheal bifurcation from the tracheal bifurcation area.

11 Claims, 10 Drawing Sheets

(56) References Cited

U.S. PATENT DOCUMENTS

| | | | |
|---|---|---|---|
| 7,366,277 B2 * | 4/2008 | Goto et al. | 378/4 |
| 7,602,970 B2 * | 10/2009 | Florin et al. | 382/173 |
| 8,229,186 B2 * | 7/2012 | Milstein et al. | 382/128 |
| 2001/0024516 A1 * | 9/2001 | Yoshioka et al. | 382/128 |
| 2002/0106116 A1 * | 8/2002 | Knoplioch et al. | 382/128 |
| 2003/0076987 A1 * | 4/2003 | Wilson et al. | 382/128 |
| 2003/0179915 A1 * | 9/2003 | Goto | 382/128 |
| 2004/0071325 A1 * | 4/2004 | Declerck et al. | 382/128 |
| 2004/0223636 A1 * | 11/2004 | Edic et al. | 382/131 |
| 2004/0249270 A1 * | 12/2004 | Kondo et al. | 600/425 |
| 2005/0185831 A1 * | 8/2005 | Rasche et al. | 382/133 |
| 2006/0171585 A1 * | 8/2006 | Rinck et al. | 382/173 |
| 2007/0049840 A1 * | 3/2007 | Odry et al. | 600/532 |
| 2007/0053478 A1 * | 3/2007 | Tsuyuki et al. | 378/4 |
| 2007/0248250 A1 * | 10/2007 | Gulsun et al. | 382/128 |
| 2008/0187199 A1 * | 8/2008 | Gulsun et al. | 382/131 |
| 2008/0253638 A1 * | 10/2008 | Binkley et al. | 382/131 |
| 2008/0273777 A1 * | 11/2008 | Luboz et al. | 382/130 |
| 2009/0060125 A1 | 3/2009 | Tsuyuki et al. | |
| 2009/0278846 A1 * | 11/2009 | Gulsun et al. | 345/423 |
| 2010/0008557 A1 * | 1/2010 | Matsumoto | 382/131 |
| 2010/0074490 A1 * | 3/2010 | Arakita et al. | 382/128 |

FOREIGN PATENT DOCUMENTS

| | | |
|---|---|---|
| JP | 2007-300966 | 11/2007 |
| JP | 2008-012171 | 1/2008 |
| JP | 2008-503303 | 2/2008 |
| JP | 2009-078126 | 4/2009 |
| JP | 2010-113607 | 5/2010 |
| WO | WO 2006/000953 A1 | 1/2006 |

OTHER PUBLICATIONS

Office Action dated Sep. 30, 2014, in Japanese Patent Application No. 2011-090948.

* cited by examiner

IMAGE PROCESSING APPARATUS AND X-RAY CT SYSTEM

CROSS-REFERENCE TO RELATED APPLICATION

This application is based upon and claims the benefit of priority from Japanese Patent Application No. 2010-113607, filed May 17, 2010 and No. 2011-090948 Filed Apr. 15, 2011; the entire contents of all of which are incorporated herein by reference

FIELD

The embodiments of the present invention relate to an image processing apparatus and an X-ray CT system.

BACKGROUND

In clinical practice, diagnosis is performed using X-ray computed tomography (CT) imaging. In an X-ray CT system, the imaging subject is irradiated with X-rays to obtain projection data based on the X-rays that pass through the imaging subject. This projection data may be referred to as a projection image.

In an X-ray CT system, at first, the imaging subject is irradiated with X-rays in small doses so that X-ray images (scanograms) are obtained as a result of transmission through the imaging subject (scanogram scan).

An engineer performs setting of imaging area, i.e., alignment of the imaging area and setting of the size of the imaging area based on the X-ray images obtained in the scanogram scan. By irradiating this imaging area with prescribed doses of X-rays, a projection image is obtained (main scan). This projection data is used in image reconstruction.

Moreover, in the following description, X-ray images are sometimes known as scanogram data.

The imaging subject includes sites accompanied with movement of the lungs or liver and other sites. Depending on these sites, it is necessary to set conditions for imaging/reconstruction.

For example, in an X-ray tomography to a heart, at first, X-ray images are captured in order to align the imaging area. Next, in order to distinguish the cardiac from other sites, it is necessary to discriminate the tracheal bifurcation, etc., on the X-ray image, and set the area for each site.

In order to automatically discriminate the cardiac position and other sites to set conditions for imaging and/or reconstruction, the tracheal bifurcation is used to discriminate the upper edge of the heart. For this purpose, this tracheal bifurcation is extracted.

In order to extract this tracheal bifurcation, threshold processing is applied on current X-ray CT images and past X-ray CT images that have been imaged using an X-ray CT system for the same patient being diagnosed, extracting the tracheal bifurcation (the former art).

Moreover, in order to emphasize and extract the outline of the lungs and heart from the X-ray images, after a smoothing process is performed on the image, the profile is analyzed vertically facing the diaphragm, to extract the thoracic vertebral area (the latter art).

The latter art proposes extracting one of the lung fields from a chest X-ray image, seeking the lower edge of the lung field within this lung field in a Y-axis direction (vertical) profile starting from a prescribed position, and searching for the thoracic vertebral area from this position of the lower edge of the lung field, by means of an X-axis direction (horizontal) profile.

However, the former art relates to X-ray CT. With X-ray CT, there is no overlapping of organs, etc., in the direction of the X-ray transmission, and the radiation dose to be irradiated to the X-ray detectors increases. Thus, the image contrast intensifies.

Hence, threshold processing of pixel values allows the tracheal bifurcation to be extracted. However, this is the CT scan, so there are problems in that the scan time is longer than a scanogram scan, and the radiation doses of the specimen (patient) increase.

Moreover, the latter art disclose the same process of extracting the lung area, but aims at extracting the thoracic vertebrae in the end. In other words, the latter art does not disclose a method of extracting the tracheal bifurcation.

DETAILED DESCRIPTION

Below, each embodiment of the image processing apparatus is described.

[First Embodiment]

Figure 1:
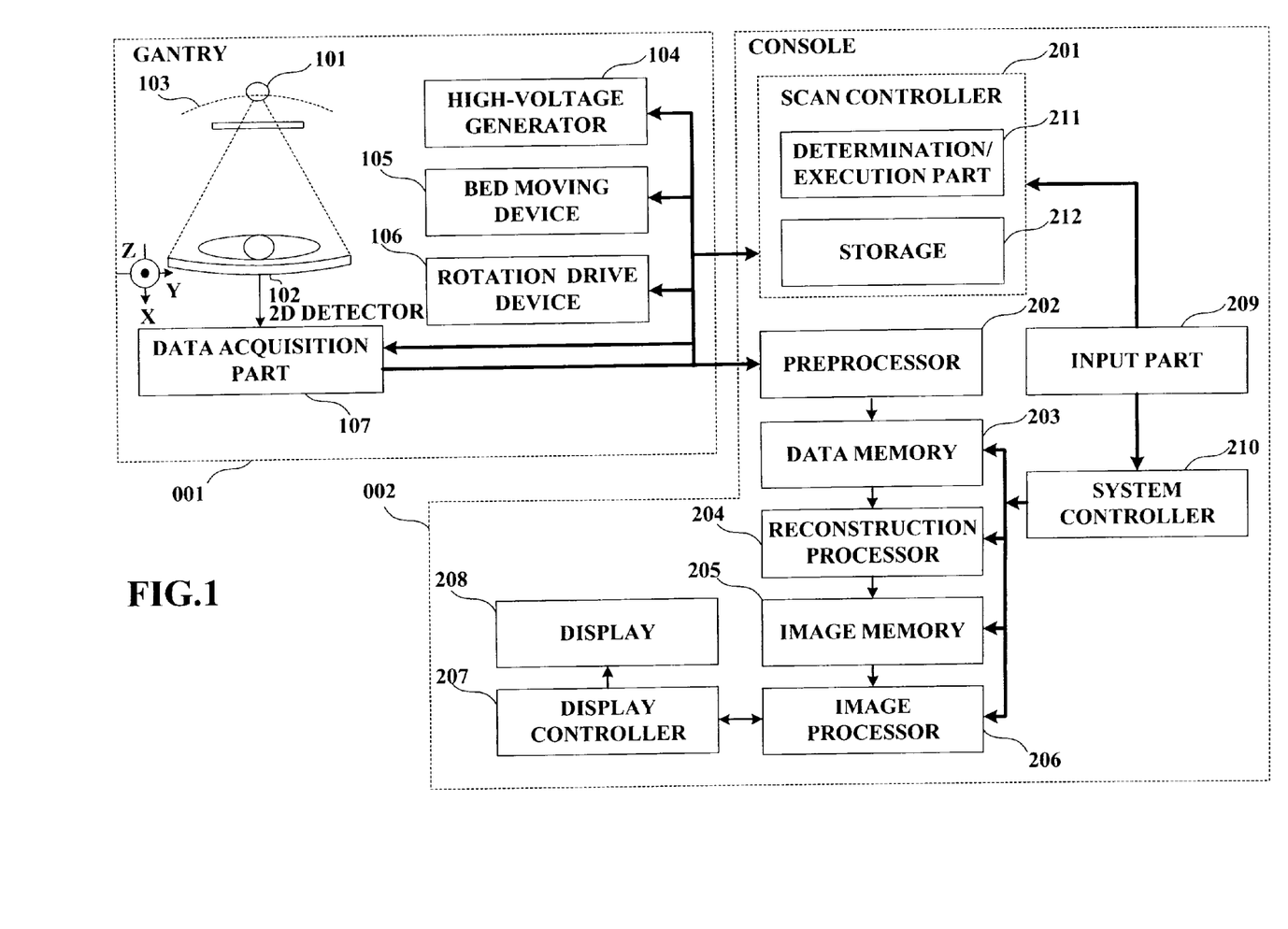
FIG. 1 is a structure diagram showing functions of the image processing apparatus according to the first embodiment.

The image processing apparatus according to the first embodiment may be, used for X-ray computed tomography apparatuses, etc. FIG. 1 is a structure diagram showing functions of the image processing apparatus according to the first embodiment. As shown in FIG. 1, the image processing apparatus of the present embodiment is provided with base device 001 (gantry) for collecting projection data related to the specimen (patient) P, a bed device (not shown in the figures) upon which the specimen P is placed, and a console 002 that controls the base device 001, performs image reconstruction processing and image display, etc., based on data collected by means of the base device 001.

The base device 001 is provided with a chassis that houses an X-ray tube 101, an X-ray detector (2D detector) 102, a rotating frame 103, a high voltage generator 104, a bed moving device 105, a rotating drive device 106, and a data acquisition system (DAS, or data acquisition part) 107.

The chassis has a diagnostic opening for the purpose of inserting specimen P. The X-ray tube 101 and the X-ray detector 102 are mounted on a ring-shaped rotating frame 103, which is driven in a rotating manner by the rotating drive device 106. Here, the rotational axis of the rotating frame 103 is defined as the Z axis. In the rotational coordinates centered around the Z axis, the axis perpendicular to the Z axis, linking the center of the detection surface of the X-ray detector 102 from the focus of the X-ray tube 101, is defined as the X axis. The Y axis is perpendicular to both the Z axis and the X axis. The bed moving device 105 is configured with a transport mechanism that transports the bed device.

The scan controller 201 controls the rotations of the rotating frame 103 through the rotating drive device 106.

The scan controller 201 controls the transport of the bed device through the bed moving device 105. By means of this control, it is possible to synchronously perform continuous transportation of the bed device during fixed speed rotation of the rotating frame 103. In this manner, the X-ray tube 101 (X-ray source) moves in a spiral relative to the specimen P, allowing a so-called helical scan which collects the projection data at several positions on this spiral trajectory. In the following text, for the convenience of explanation, there may be cases in which the scan controller 201 directly controls the rotating frame 103 and the bed device.

Below, a series of data processing is described, including: setting a plurality of imaging areas based on the scanogram data obtained by means of a scanogram scan; additionally, performing the main scan based on the set imaging areas; and additionally, performing image reconstruction using the projection data obtained by means of the main scan.

Moreover, the series of the data processing is not limited to a helical scan, but can be applied to a so-called dynamic scan, in which projection data is collected continuously with the bed device in a stationary state.

Additionally, it can also be applied to a conventional scan, in which the projection data corresponding to one rotation is collected, with the bed device in a stationary state at a certain position, subsequent to which, after the bed device has moved and stopped, the operation of collecting the projection data for one rotation at the next position is repeated.

Below, one example is described that is applicable to a helical scan, and in particular, to a multihelical scan, which is a simultaneous collection of multi-array detectors.

Subsequent to that, one example is described as applied to conventional scans.

(One Example Applied to Multihelical Scans)

The rotating frame 103 is rotated by means of the rotating drive device 106, under the control of the scan controller 201. Accompanying this rotation of the rotating frame 103, the X-ray tube 101 and the X-ray detector 102 are rotated around the specimen P. Under the control of the scan section 201, when a high voltage is applied to the X-ray tube 101 from the high voltage generator 104, X-rays are generated from the X-ray tube 101. The X-rays that are generated by the X-ray tube 101 and pass through the specimen are detected by the X-ray detector 102, and collected by the data acquisition system (DAS) 107 as projection data. Additionally, the rotating frame 103, similar to the chassis, has an opening in its central part. At the time of scanning, the specimen P, which is placed on top of the bed device, is inserted into that opening.

X-ray tube voltage is applied between the negative pole and the positive pole of the X-ray tube 101 from the high voltage generator 104. A filament current (X-ray tube current) is supplied to the filament of the X-ray tube 101 from the high voltage generator 104. By means of applying the X-ray tube voltage and supplying the filament current, X-rays are generated from the target of the positive pole of the X-ray tube 101.

The X-ray detector 102 is for the purpose of detecting X-rays that have passed through the specimen P.

The X-ray detector 102 may be either a multi-slice type (multiple array type) or a single-slice type (single array type).

Here a multi-slice type detector, which has a radiation reduction effect, is explained. In the X-ray detector 102, the detecting elements which detect X-rays are respectively and multiply disposed in the channel direction (close to the Y axis) and the slice direction of the specimen (Z axis direction). For example, a plurality of X-ray detecting elements are disposed such that approximately 600 to 1000 elements are in the channel direction, and approximately 24 to 256 columns are in the slice direction.

In the present embodiment, a plurality of X-ray detecting elements having a light reception surface in the form of a 0.5 mm×0.5 mm square, are disposed with 1000 elements in the channel direction and 64 columns in the slice direction, forming a multi-array detector. Each detecting element has a scintillator and a photodiode chip (not shown in the figures). The X-ray detector 102 may be either a multi-slice type detector, in which detecting elements of a uniform size are disposed in the slice direction, or an uneven pitch multi-slice detector, in which detecting elements of varying sizes are multiply disposed in the slice direction.

The data acquisition system (DAS) 107 converts signals output to each channel from the X-ray detector 102 into voltage signals, amplifies them, and further converts them into digital signals. These converted digital signals (also known as "pure raw data") are supplied to the console 002 on the exterior of the base device 001.

The preprocessor 202 of console 002 performs corrective processing, such as offset correction, reference correction and sensitivity correction, on the data (pure raw data) output from the data acquisition system (DAS) 107.

The preprocessed pure raw data is generally referred to as raw data. Here, pure raw data and raw data are collectively referred to as "projection data". The projection data is stored in the data storage section (data memory) 203 of the console 002. The data includes scanogram data obtained by means of scanogram scans, and projection data obtained by means of the main scan.

In the tracheal bifurcation identification processing, the imaging area setting processing, and the image reconstruction area setting processing described below, scanogram data is used, while for image reconstruction, projection data is used.

The console 002, along with the above-mentioned preprocessor 202 and the data storage section 203, has a scan controller 201, a reconstruction processor 204, an image storage section (image memory) 205, an image processor 206, a display controller 207, a display section (display) 208, an input device 209, and a system controller 210.

The reconstruction section 204 performs image reconstruction based on the selected or collected projection data set (scan data set). As examples of projection data sets, other than projection data, bed device position information and rotational angle information of the rotating frame 103, which are supplementary data, are included.

In the reconstruction processor 204, data that has been reconstructed in this manner is stored in the image storage section 205, and is sent to the image processor 206 to perform processing that is suitable for image display.

The image processor 206 performs tracheal bifurcation area extraction processing on the projection data stored in the data storage section 203. The image processor 206 performs the following on the projection data after extraction processing on the tracheal bifurcation area, which is: tracheal bifurcation identification processing; imaging area setting processing; and image reconstruction area setting processing. The image processor 206 outputs the projection data that has been processed to the display controller 207. The image processor 206 is an example of a "tracheal bifurcation area extraction part", a "tracheal bifurcation identification part", an "imaging area setting part" and an "image reconstruction area setting part".

The display controller 207 causes the display section 208 to display the projection data input from the image processor 206.

The system controller 210 performs a general control of the image processing apparatus, namely the control of the reconstruction processor 204, the image storage section 205, and the image processor 206, etc.

Figure 2:
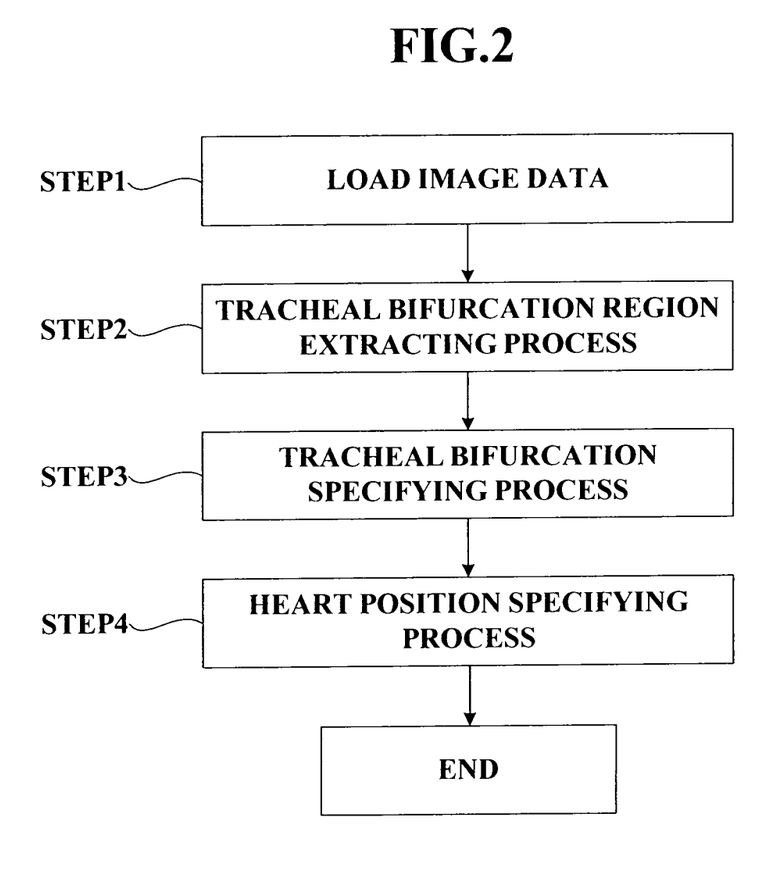
FIG. 2 is a flow chart showing an outline of the processing in the image processing apparatus.

Next, in the helical scan, the processing from the reading of the scanogram data to the identification of the position of the heart based on the scanogram data is explained, referring to FIG. 2. FIG. 2 is a flow chart showing an outline of the processing in the image processing apparatus.

[Step 1: Imaging and Reading of Scanogram Data]

By means of the image processing apparatus shown in FIG. 1, the chest X-ray images obtained by scanogram scans are read, and stored in the data storage section 203.

Specifically, at first, information about the specimen is entered using input devices 209 such as a keyboard or touch panel, etc. When information about the specimen is entered, imaging conditions corresponding to the examination site (X-ray tube voltage, X-ray tube current, imaging time, imaging area, attached filters, etc.) are displayed on the display section 208 through the image processor 206.

Next, when the imaging switch is pressed, a high voltage is applied to the X-ray tube 101 by means of the high voltage generator 104, and X-rays are generated from the X-ray tube 101. The generated X-rays are irradiated on to the specimen P. The X-rays that pass through the specimen P are irradiated to the X-ray detector 102. From the X-ray detector 102, scanogram data (X-ray image) is input into the data acquisitions system (DAS) 107. The data acquisition center (DAS) 107 sends the scanogram data to the preprocessor 202. The preprocessor 202 sends the scanogram data to the data storage section 203.

[Step 2: Tracheal Bifurcation Area Extraction Processing]

In Step 2, the tracheal bifurcation area is extracted.

This is explained below, using FIG. 2.

[Step 2-1: Tracheal Bifurcation Area Extraction Processing]

With respect to the scanogram data, the vertical profile and the horizontal profile of the scanogram data stored in the data storage section 203 are analyzed to extract the image characteristic quantities of the tracheal bifurcation area (mean value of the pixel values, median, mode, maximum value, minimum value). Then, gradation processing is performed so that these image characteristic quantities reach the target values, to extract an outline of the lungs (lung apex, lung base, etc.).

From the lung outline and the cardiac area (upper edge), the tracheal bifurcation area is extracted, using the method above.

[Step 3: Tracheal Bifurcation Identification Processing]

Figure 3:
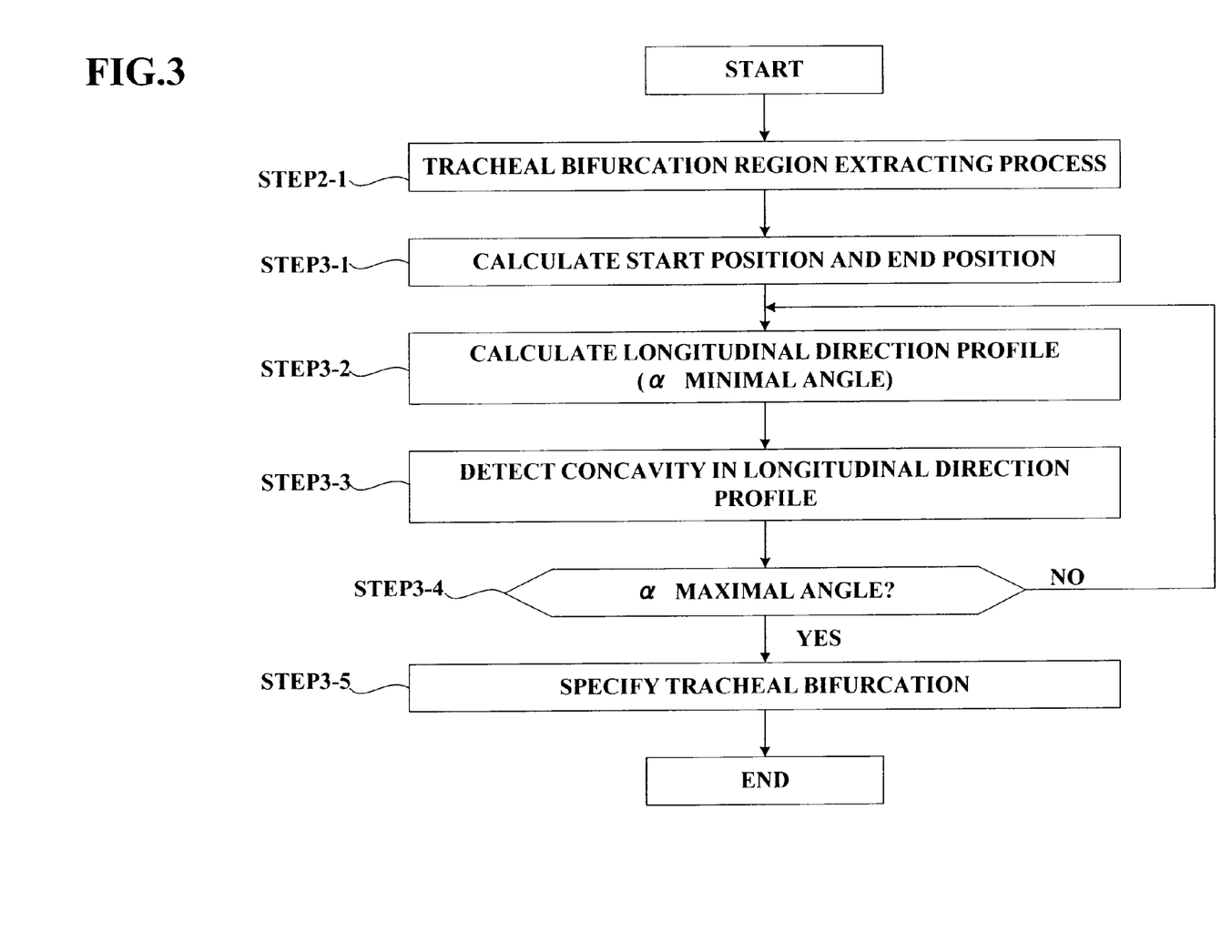
FIG. 3 is a flow chart showing a processing of tracheal bifurcation area extraction processing.

In Step 3, the tracheal bifurcation is identified. This is explained below, using FIG. 3.

[Step 3-1: Starting Position Calculation Processing, Finishing Position Calculation Processing]

In order to identify the tracheal bifurcation from the tracheal bifurcation area obtained in Step 2-1, the starting position calculation section derives by calculation the starting position coordinates (Xg, Yg) at which the computational processing of the vertical profile (profile in the body axis direction) is started, which will be explained later. The starting position coordinates may be set to a suitable position. In other words, for example, it is possible to set, as the starting position coordinates, an arbitrary position on a virtual extension line of a central line passing through approximately the center of an approximate cross-section of the left bronchus or the left bronchus in the tracheal bifurcation area extracted by Step 2-1.

The finishing position calculation section derives by calculation the finishing position coordinates (Xh, Yh) at which the computational processing of the vertical profile is finished, which will be explained later. The finishing position coordinates may be set to a suitable position. In other words, for example, it is possible to set, as the finishing position coordinates, an arbitrary position on a virtual extension line of a central line passing through approximately the center of an approximate cross-section of the left bronchus or the left bronchus in the tracheal bifurcation area extracted by Step 3-1.

[Step 3-2: Vertical Profile (Body Axis Profile) Computational Processing]

Figure 4:
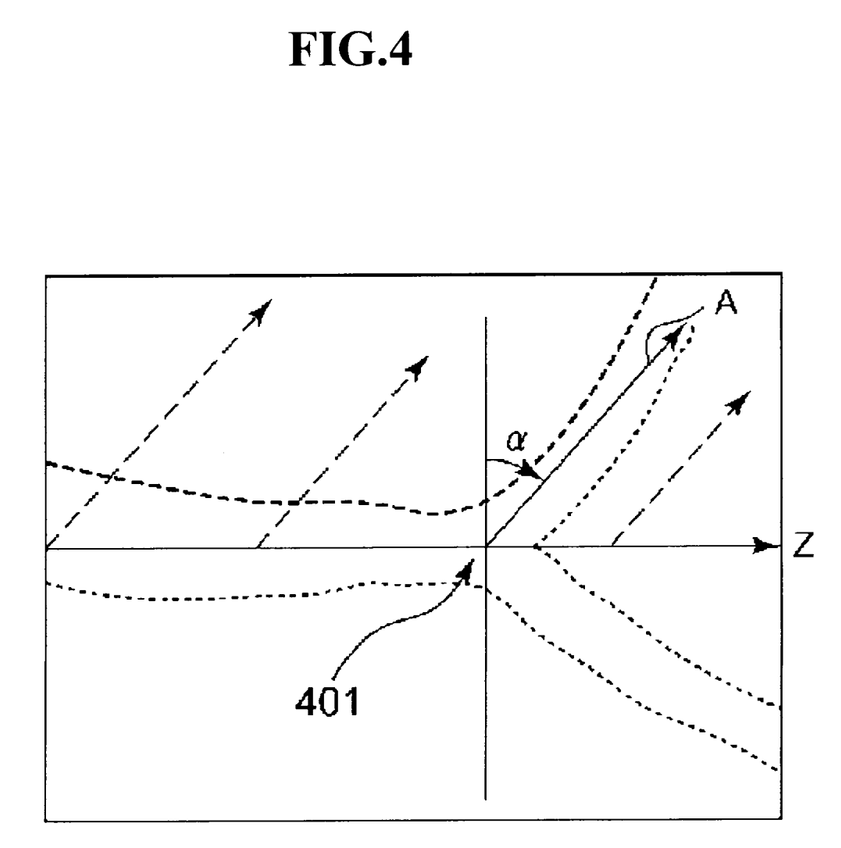
FIG. 4 is an outline diagram showing a direction of a vertical profile.

FIG. 4 is an outline diagram showing the computational direction of a vertical profile (body axis profile). This figure shows the tracheal bifurcation 401, the A direction and the angle α direction. The pixel values in a direction along the A direction (angle α direction) in this figure are cumulated to create a vertical profile (body axis profile). In the present embodiment, the A direction refers to a direction along the running direction of the left bronchus. For example, with an accumulation to a 45° direction, a vertical profile (org30_prfl[ ]) is created.

As shown in FIG. 4, a plurality of vertical profiles may be computed. Moreover, the bronchus may be either the left bronchus or the right bronchus as the standard. The left bronchus is preferable as the standard. It is preferable that the pixel values are accumulated in the direction of an inclination of 30° to 80°, perpendicular to the body axis longitudinal direction of the specimen P from the starting position coordinates (Xg, Yg) to the finishing position coordinates (Xh, Yh) that were derived in Step 3-1 and Step 3-2, and a vertical profile is computed.

In FIG. 4, the angle between the direction perpendicular to the body axis longitudinal direction of specimen P and the accumulated direction is identified as α.

For the left bronchus, it is preferable for a to be set in a range of 30° to 60°, and approximately 45° is even more preferable. For the right bronchus, it is preferable for a to be set in a range of 50° to 80°, and approximately 65° is even more preferable. In the present embodiment, a may be set from the minimum value to the maximum value, and within that range, for each prescribed angle, a vertical profile may be created. In particular, a may be set from 30° (minimum value) to 60° (maximum value), and for every 5° from the minimum value to the maximum value, a vertical profile may be created.

The accumulated vertical profiles are convoluted with a smoothing kernel to create a variation curve for the smoothed vertical profiles. For example, the abovementioned vertical profiles that were accumulated to a 45° direction (org45_prfl[ ]) are convoluted with a smoothing kernel (smth45_prfl[ ]) to create a variation curve for the smoothed vertical profiles. For example, smth45_prfl={0.1, 0.2, 0.4, 0.2, 0.1} is created.

The variation curve of the smoothed vertical profiles is convoluted with a differential kernel to create a differential kernel (dif_prfl[ ]). The kernel length depends on the pixel size, and can be modified appropriately. For example, if the pixel size is 2.0 mm, as a differential kernel, dif_kernel={0.0, 0.0, 0.0, 1.0, 1.0, 1.0, −1.0, −1.0, −1.0, −2.0, −2.0, −2.0, −1.0, −1.0, −1.0, 1.0, 1.0, 1.0, 2.0, 2.0, 2.0} is created.

Figure 5:
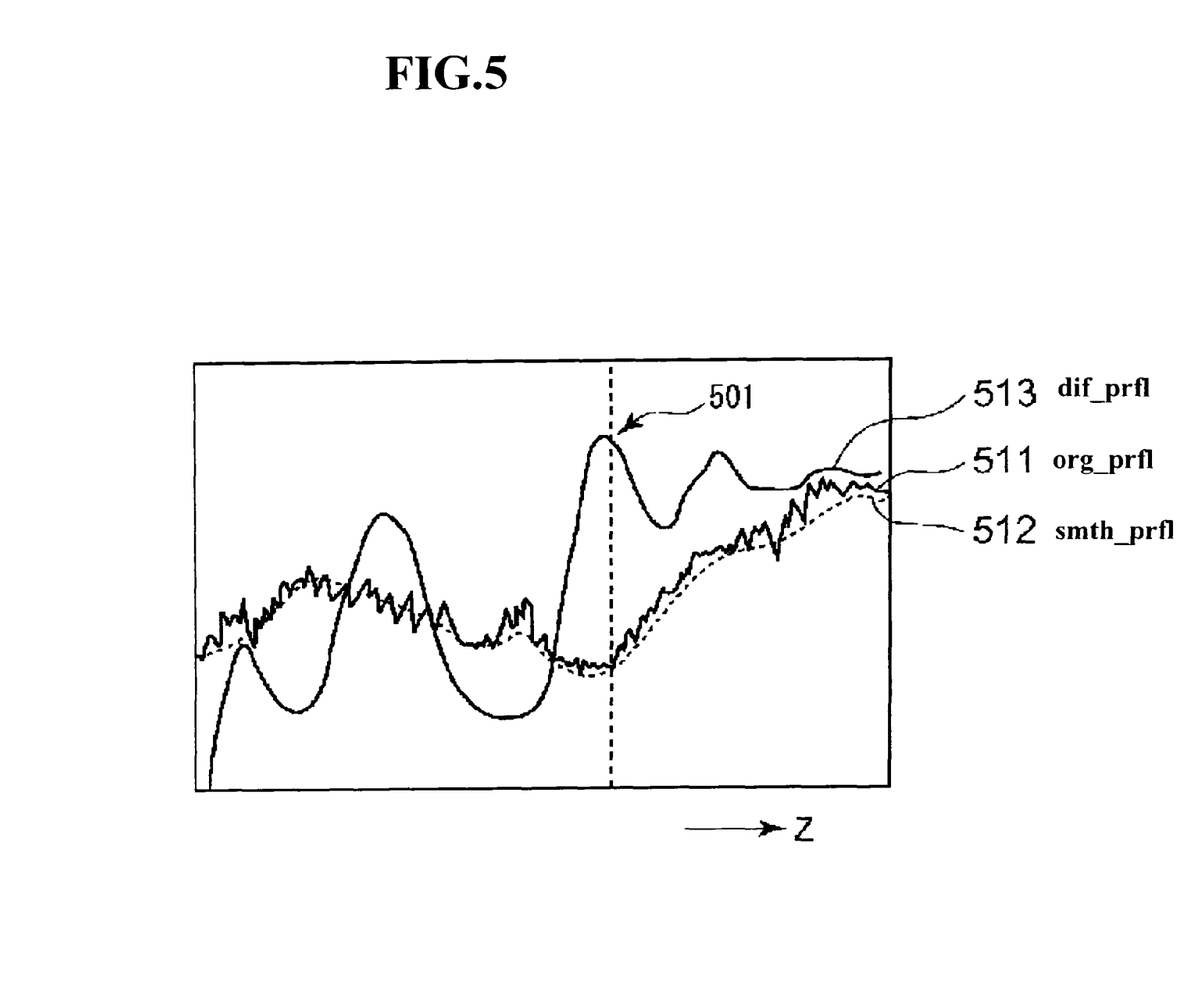
FIG. 5 is an outline diagram showing a concave portion of accumulated value of the vertical profiles.

FIG. 5 is an outline diagram of the variation curve of the vertical profiles computed in FIG. 4. In FIG. 5, the position corresponding to the tracheal bifurcation 401 is shown as 501. In FIG. 5, the variation curve of the vertical profiles that have undergone cumulative processing, the variation curve of the vertical profiles that have undergone smoothing processing, and the variation curve of the vertical profiles that have undergone differential processing are shown as 511 to 513.

[Step 3-3]

Perform concave portion detection processing on the vertical profiles up to the largest angle.

[Step 3-4]

Determine whether a is the maximum value or not; if NO, then return to Step 3-2, but if YES, then proceed to Step 3-5.

[Step 3-5: Tracheal Bifurcation Identification Processing]

By creating the differential kernel, it is possible to clarify the concave portions in the variation curve of the vertical profiles, and to identify the tracheal bifurcation.

In other words, for each angle α, the angle between the direction perpendicular to the body axis longitudinal direction of specimen P and the accumulated direction, the position in which the differential kernel shows the maximum value is set as the point at which the trachea bifurcates, and the tracheal bifurcation is identified. In particular, the position 501, which is the peak of the curve 513, on which the differential kernel processing in FIG. 5 has been performed, shows a concave shape, and is the position corresponding to the tracheal bifurcation.

In the present embodiment, a variation curve may be created for the vertical profiles in which a is from the minimum value to the maximum value, and the position at which the differential kernel (dif_prfl[ ]) is the maximum may be identified as the tracheal bifurcation.

[Step 4: Cardiac Position Identification Processing]

Moreover, from the positions of the tracheal bifurcation and the lung base, processing to identify the position of the heart may be performed. At the time of this identification processing, various forms of filter processing, pattern matching processing, etc., may be used.

The tracheal bifurcation is identified by the abovementioned method, and the lung base is identified as described. At the time of this identification of the lung base, the left and right lung field areas may be used, and the vertical profiles and horizontal profiles may be used.

[Second Embodiment]

In the above description, for the helical scan, the processing is explained, from the reading (Step 1) of the scanogram data obtained by a scanogram scan, until the identification (Step 4) of the cardiac position based on the scanogram data. It should be noted that the identification of the cardiac position may be performed based on the projection data (transmission X-ray images which are not reconstructed) from the helical scan described below.

Figure 6A:
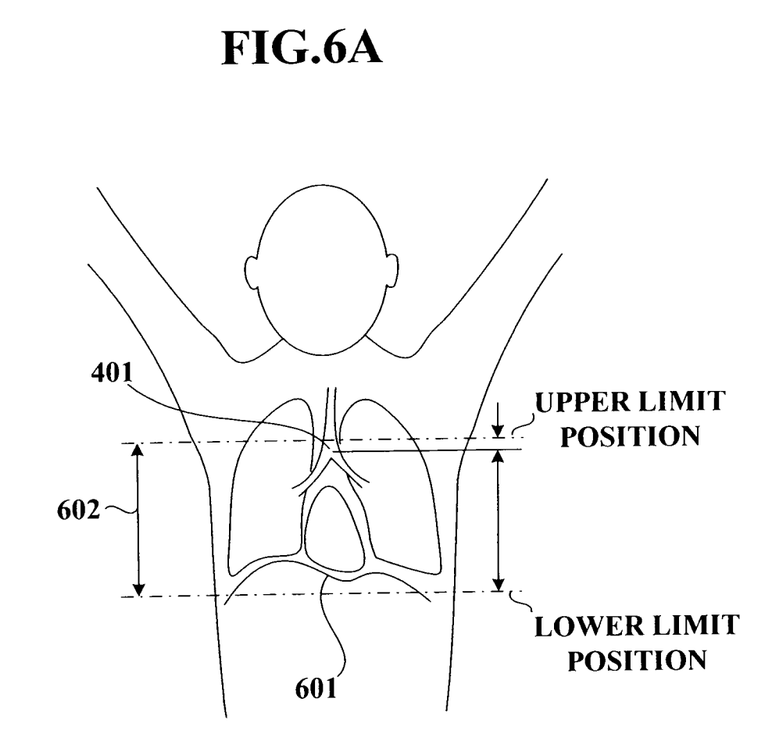
FIG. 6A is a diagram showing an identified cardiac position according to a second embodiment.
Figure 6B:
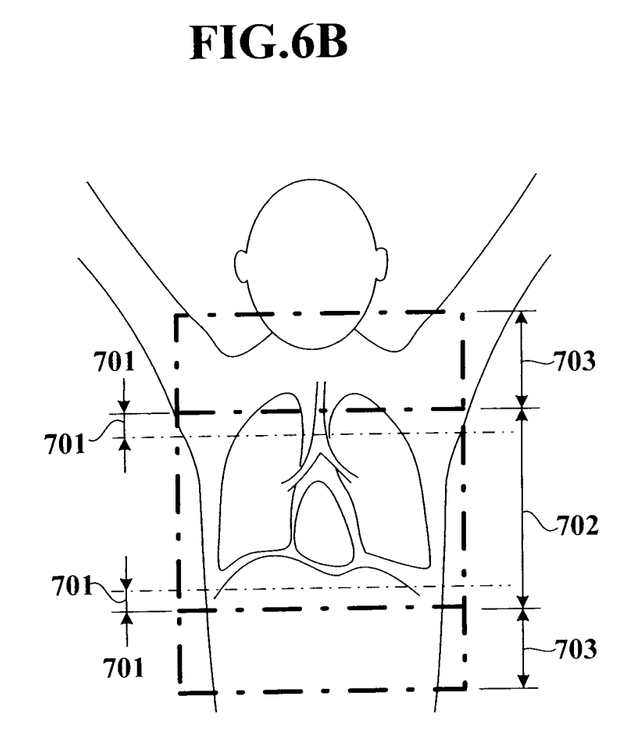
FIG. 6B is a diagram in which the set imaging ranges are shown as a dashed-dotted line.
Figure 6C:
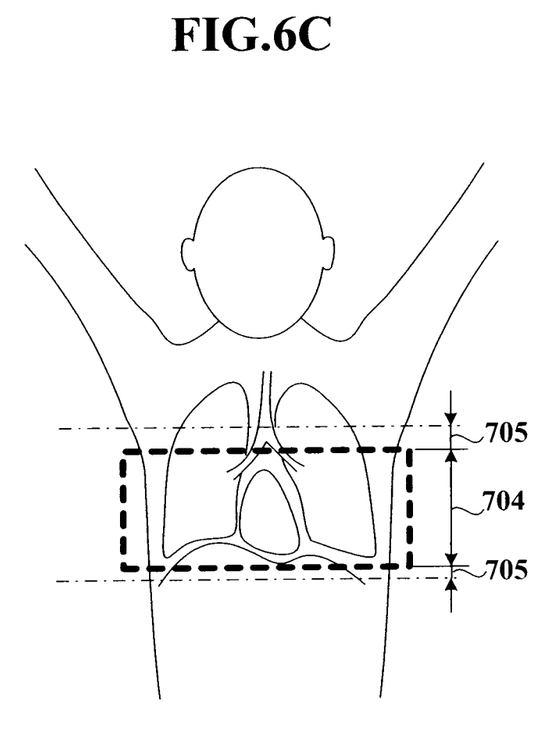
FIG. 6C is a diagram showing the area for performing image reconstruction as a dotted line.

Next, one example of the processing for the helical scan is explained referring to FIG. 6A to FIG. 6C, in which the imaging area is set based on the identified cardiac position and image reconstruction is performed using the projection image (projection data) obtained from the main scan based on this imaging area. It should be noted that the cardiac position 602 in FIG. 6A indicates a range from the coronary artery of the heart (upper limit) to the lower position of the ventricles (lower limit).

FIG. 6A is a diagram showing the identified cardiac position 602. As shown in FIG. 6A, the cardiac position 602 is identified from the tracheal bifurcation position 401.

Moreover, the cardiac position 602 may also be identified from the lung base position 601.

The image processor 206, by having a margin 701 above and below the identified cardiac position 602, sets the imaging area when imaging the cardiac position and other imaging areas. In this manner, a area that includes the cardiac position 602 and the margins 701 is set as the imaging area when imaging the cardiac region 602. The imaging area when imaging the cardiac position is a area (cardiac-gated imaging area) 702 for performing cardiac-gated imaging for the purpose of computing the movement amount of the heart. Moreover, the method of having a margin is not limited to this. For example, from the tracheal bifurcation position 401, a position that is separated by about half the diameter of the bronchus in the downward direction may be set as the upper cardiac position, and from that position, a prescribed margin above and below may be established.

The display controller 207 causes the display section 208 to display the cardiac-gated imaging area 702 and other imaging areas 703, overlapping the scanogram data.

One example of the "display section" is represented by the display controller 207 and the display section 208.

Since the display section 208 displays the cardiac-gated imaging area 702 and other imaging areas 703, the surgeon is able to check the cardiac-gated imaging area 702.

FIG. 6B is a diagram in which the set imaging ranges 702 and 703 are shown as a dashed-dotted line.

Based on the cardiac-gated imaging area 702, a projection image is obtained from the main scan. The image processor 206 sets the area (phase computation area 704) for deriving the reconstruction phases based on the information of the tracheal bifurcation position 401. The phase computation area 704 is set to be narrower than the cardiac-gated imaging area 702.

The display controller 207 causes the display section 208 to display the phase computation area 704 overlapping the scanogram data. One example of the "display section" is represented by the display controller 207 and the display section 208. By displaying the phase computation area 704 on the display section 208, the surgeon is able to check the phase computation area 704.

FIG. 6C is a diagram showing the area for performing image reconstruction 704 as a dotted line. As shown in FIG. 6C, the phase computation area 704, is a area in which only a fixed width 705 portion of the upper area and the lower area of the cardiac-gated imaging area 702 are reduced.

Moreover, the phase computation area 704 may be set to be wider than the cardiac-gated imaging area 702, or set to match the cardiac-gated imaging area 702.

The image processor 206 performs cardiac-gated reconstruction based on the projection image of the phase computation area 704. In particular, additive processing is performed on the projection image to derive the movement amount of the entire heart using the cardiac phase interval to determine the cardiac phase with a small movement amount (optimal phase) to perform image reconstruction based one the determined optimal phase.

[Third Embodiment]

(Examples Applied to a Conventional Scan)

Now, an example of the process of image reconstruction in a conventional scan, by setting a cardiac-gated imaging area 702 and other imaging areas 703 based on the identified cardiac position 602, and processing the projection image (projection data) obtained by scanning based on the imaging areas 702 and 703, is described with reference to FIG. 7A to FIG. 7D. In addition, in the example of a conventional scan described below, the cardiac-gated imaging area 702 and other imaging areas 703 are set to the same width. In addition, the cardiac-gated imaging area 702 and the other imaging areas 703 may be set to different widths.

Figure 7A:
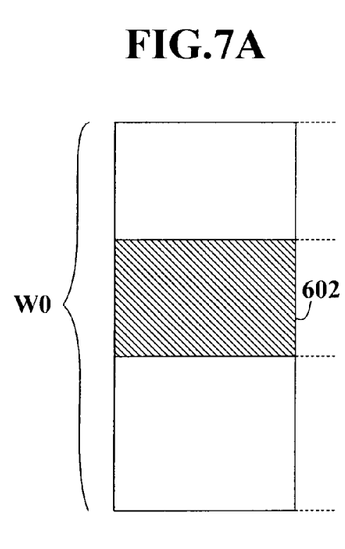
FIG. 7A shows an entire imaging area according to a third embodiment.

FIG. 7A shows the entire imaging area. As shown in FIG. 7A, the cardiac position 602 is included in the width W0 of the entire imaging area.

Figure 7B:
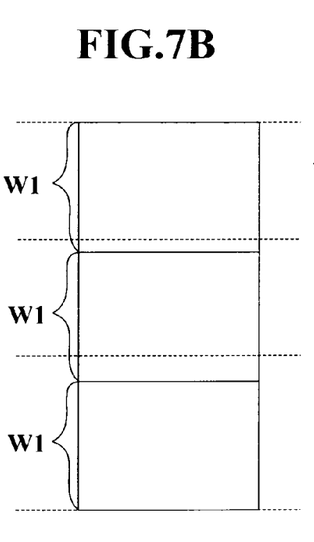
FIG. 7B shows an entire imaging area divided into three, with three imaging areas.

FIG. 7B shows the entire imaging area divided into three, with three imaging areas. As shown in FIG. 7B, the cardiac position 602 is located spanning two out of three imaging areas. In addition, the width of the entire imaging area is set to be W0 and each width of each imaging area is set to be W1.

Figure 7C:
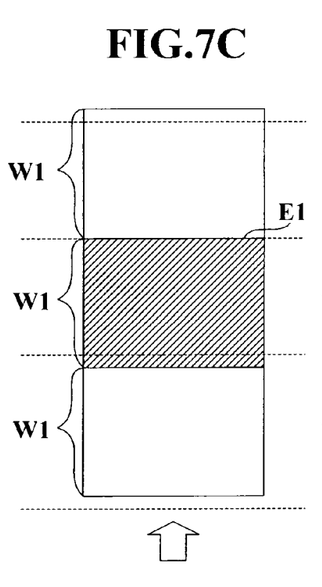
FIG. 7C shows the state in which movement is performed without changing the width of each imaging area.

FIG. 7C shows the state in which movement is performed without changing the width of each imaging area.

The image processing part 206 moves each imaging area in the arrow direction shown in FIG. 7C so that one imaging area covers the cardiac position 602. With the movement of each imaging area, as shown in FIG. 7C, the cardiac position 602 is located so as to be within one imaging area.

Because each imaging area is moved, three imaging areas cannot cover the entire imaging area with the width of the imaging area W1 as it is.

Figure 7D:
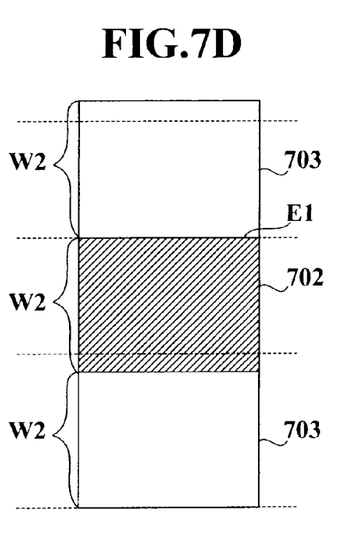
FIG. 7D shows a state in which the width of each imaging area is changed so as to include the entire imaging area.

FIG. 7D shows a state in which the width of each imaging area is changed so as to include the entire imaging area. As shown in FIG. 7D, the image processor 206 enlarges the width of the imaging area from W1 to W2 so that the entire imaging area is covered with three imaging areas. In addition, when enlarging the width of the imaging area, it is performed without moving the position of E1 which is one end of the imaging area that covers the cardiac position 602.

The imaging area that covers the cardiac position 602 becomes the imaging area of the cardiac-gated imaging area 702. Imaging areas other than that become non-cardiac-gated imaging areas 703.

[Fourth Embodiment]

(Other Examples Applied to a Conventional Scan)

The third embodiment shows an example of cardiac-gated reconstruction of the entire heart using the projection image obtained by moving each imaging area in a conventional scan so that one imaging area covers the cardiac position 602 and scanning based of the imaging areas 702 and 703 after the movement.

In addition, although for the cardiac-gated reconstruction of the entire heart, the optimal phase, which is determined based on the movement amount of the entire heart, for the cardiac-gated reconstruction of the partial heart, an optimal phase which is determined based on the movement amount of the partial heart is used in order to make the image of the partial heart clear.

With reference to FIG. 8A to FIG. 8E, the fourth embodiment describes an example of cardiac-gated reconstruction of the cardiac chambers using an optimal phase that is determined based on the movement amount of a part of the heart.

Figure 8A:
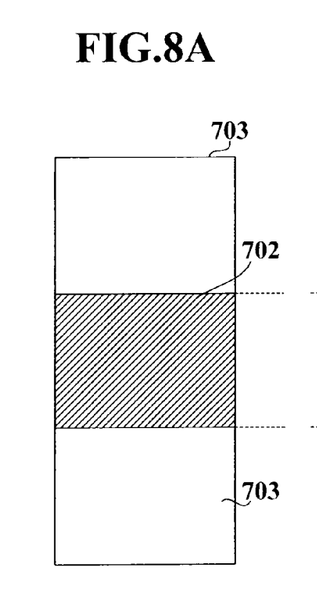
FIG. 8A shows a planned imaging area according to the fourth embodiment.
Figure 8B:
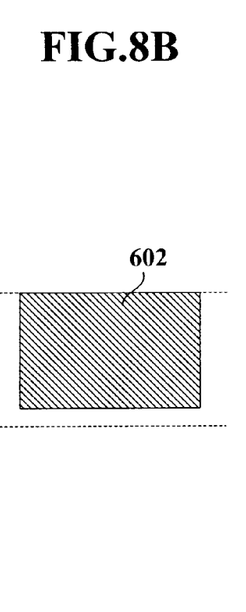
FIG. 8B shows a cardiac position.

FIG. 8A shows the cardiac-gated imaging area and non-cardiac-gated imaging area. Furthermore, FIG. 8B shows the cardiac position 602.

Figure 8C:
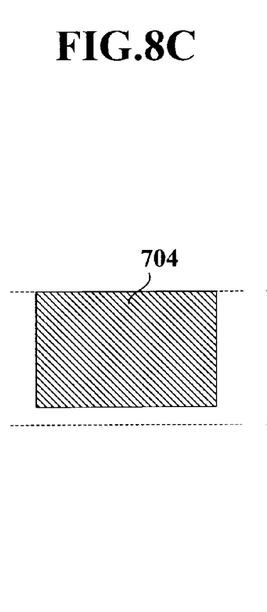
FIG. 8C shows a area for computing a cardiac-gated reconstruction phase when imaging a coronary artery.

FIG. 8C shows the area for computing the cardiac-gated reconstruction phase when imaging the coronary artery. The image processor 206 sets the phase calculation area to the same area as the cardiac position 602. As shown in FIG. 8B and FIG. 8C, the phase calculation area 704 matches the range showing the cardiac position 602.

The image processor 206 refers to the tracheal bifurcation position 401 as a standard to calculate the position of the cardiac chambers based on an experimental rule in that it corresponds to the body type of the specimen.

Figure 8D:
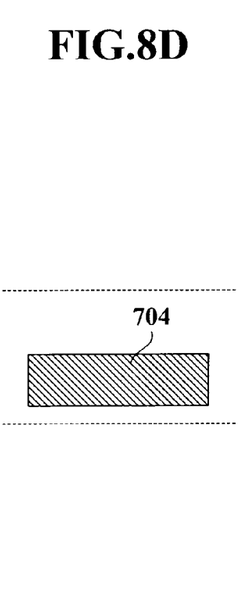
FIG. 8D shows a area for calculating a cardiac-gated reconstruction phase when imaging a cardiac muscle.

FIG. 8D shows the area for calculating the cardiac-gated reconstruction phase when imaging the cardiac muscle. The image processing apparatus 206 sets the phase calculation area 704 to the same area as the position of the cardiac chambers. FIG. 8D shows the phase calculation area 704 corresponding to the same area as the location of the cardiac chambers.

Based on the above, it is possible to calculate each optimal phase from the phase calculation area 704 in both cases of imaging the coronary artery and imaging cardiac muscle.

Figure 8E:
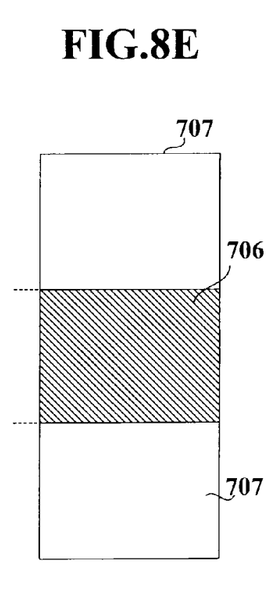
FIG. 8E shows a cardiac-gated reconstruction area and a non-cardiac-gated reconstruction area.

FIG. 8E shows the cardiac-gated reconstruction area 706 and the non-cardiac-gated reconstruction area 707.

The image processor 206 performs cardiac-gated reconstruction (as mentioned above), based on the projection image (projection data) of the phase calculation area 704, which is set to the same area as the cardiac position 602. Furthermore, cardiac-gated reconstruction (as mentioned above) of the cardiac chambers is performed, based on the projection image (projection data) of the phase computation area 704, which is set to the same area as the location of the cardiac chambers. In addition, the optimal phase at this time may be cardiac phases with less movement, upon calculation of the movement amount of the cardiac chambers.

The image processing apparatus according to the present embodiment allows images such as the heart (coronary artery) to be processed. In other words, the present embodiment allows the cardiac position (coronary artery) to be set automatically and set as the imaging area.

Furthermore, at the time of image reconstruction, a reconstruction area, such as the cardiac position (coronary artery) can be set automatically. Furthermore, during cardiac-gated imaging, using the image processing apparatus according to this embodiment allows the amount of cardiac movement (coronary artery) to be calculated and the accuracy of optimal phase detection to be increased.

While certain embodiments have been described, these embodiments have been presented by way of example only, and are not intended to limit the area of the inventions.

Indeed, the novel embodiments described herein may be embodied in a variety of other forms; furthermore, various omissions, substitutions and changes in the form of embodiments described herein may be made without departing from the spirit of the inventions. The accompanying Claims and their equivalents are intended to cover such forms or modifications as would fall within the area and spirit of the inventions.

What is claimed is:

1. An image processing apparatus, comprising:
   a tracheal bifurcation area extraction part configured to extract a tracheal bifurcation area from an X-ray transmission image of a subject; and
   a tracheal bifurcation identification part configured to identify a tracheal bifurcation from the tracheal bifurcation area,
   wherein the tracheal bifurcation identification part is configured to compute multiple vertical profiles, each vertical profile accumulated from pixel values lying on a line having a prescribed non-zero angle with a body axis of the subject in the tracheal bifurcation area, and to detect a concave portion in a curve derived from the computed vertical profiles to identify the tracheal bifurcation.

2. The image processing apparatus of claim 1, wherein the tracheal bifurcation area extraction part is configured to extract the tracheal bifurcation area from an outline of lungs and/or a heart.

3. The image processing apparatus of claim 1, wherein the tracheal bifurcation identification part is configured to identify positions of subject organs from the identified tracheal bifurcation.

4. The image processing apparatus of claim 1, wherein, with the identified tracheal bifurcation as a basis, an imaging area and/or an image reconstruction area is set.

5. An X-ray CT system that collects X-ray transmission images of a subject, and is configured to reconstruct images displaying a structure of an interior of the subject based on the collected X-ray transmission images, comprising:
   a tracheal bifurcation identification part configured to determine positional information of a tracheal bifurcation from the collected X-ray transmission images as scanogram data obtained from a scanogram scan; and
   an imaging area setting part configured to set an imaging area based on the positional information of the tracheal bifurcation obtained from the collected X-ray transmission images,
   wherein the tracheal bifurcation identification part is configured to compute multiple vertical profiles, each vertical profile accumulated from pixel values lying on a line having a prescribed non-zero angle with a body axis of the subject in the tracheal bifurcation area, and to detect a concave portion in a curve derived from the computed vertical profiles to determine positional information of a tracheal bifurcation.

6. The X-ray CT system of claim 5, further comprising a display configured to display the X-ray transmission images, wherein the display is configured to display the set imaging area overlapping the X-Ray transmission images.

7. An X-ray CT system that collects X-ray transmission images of a subject and is configured to reconstruct images displaying a structure of an interior of the subject based on the collected X-ray transmission images, comprising:
   a tracheal bifurcation identification part configured to determine positional information of a tracheal bifurcation from the X-ray transmission images; and
   an image reconstruction area setting part configured to set an image reconstruction area based on the positional information of the tracheal bifurcation obtained from the X-ray transmission images,
   wherein the tracheal bifurcation identification part is configured to compute multiple vertical profiles, each vertical profile accumulated from pixel values lying on a line having a prescribed non-zero angle with a body axis of the subject in the tracheal bifurcation area, and to detect a concave portion in a curve derived from the computed vertical profiles to determine positional information of a tracheal bifurcation.

8. The X-ray CT system of claim 7, further comprising a display configured to display the X-ray transmission images, wherein the display is configured to display the set image reconstruction area overlapping the X-ray transmission images.

9. An X-ray CT system that collects X-ray transmission images of a subject, and is configured to reconstruct images displaying a structure of an interior of the subject based on the collected X-ray transmission images, comprising:
   a tracheal bifurcation identification part configured to determine positional information of a tracheal bifurcation from the X-ray transmission images;
   an imaging area setting part configured to, based on the positional information of the tracheal bifurcation, determine at least one area from between an upper area and a lower area of a heart, and set the determined at least one area as an image reconstruction area; and
   an image processing part configured to, based on an X-ray transmission image of the upper area or the lower area of the heart, determine an amount of movement in the upper area or the lower area of the heart, and further determine a cardiac pulse phase with a small amount of movement,
   wherein the tracheal bifurcation identification part is configured to compute multiple vertical profiles, each vertical profile accumulated from pixel values lying on a line having a prescribed non-zero angle with a body axis of the subject in the tracheal bifurcation area, and to detect concave portions in the computed vertical profiles to determine positional information of a tracheal bifurcation.

10. The X-ray CT system of claim 9, further comprising a display configured to display the X-ray transmission images, wherein the display is configured to display the set image reconstruction area overlapping the X-ray image.

11. The image processing apparatus of claim 1, wherein the tracheal bifurcation area extraction part is configured to extract the tracheal bifurcation area from the X-ray transmission image, which is obtained from a scanogram scan of the subject.

* * * * *